US012667337B2

(12) United States Patent
Takahashi

(10) Patent No.: US 12,667,337 B2
(45) Date of Patent: Jun. 30, 2026

(54) ULTRASONOGRAPHY APPARATUS, ULTRASONOGRAPHY METHOD, AND ULTRASONOGRAPHY PROGRAM FOR SHOWING IMAGE OF SUBJECT BASED ON ULTRASOUND PROBE

(71) Applicant: FUJIFILM Corporation, Tokyo (JP)

(72) Inventor: Azuma Takahashi, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 19/007,535

(22) Filed: Jan. 1, 2025

(65) Prior Publication Data

US 2025/0127490 A1 Apr. 24, 2025

Related U.S. Application Data

(63) Continuation of application No. 18/173,071, filed on Feb. 23, 2023, now Pat. No. 12,239,487, which is a
(Continued)

(30) Foreign Application Priority Data

Sep. 11, 2020 (JP) ................................. 2020-153150

(51) Int. Cl.
*A61B 8/00* (2006.01)

(52) U.S. Cl.
CPC ............ *A61B 8/463* (2013.01); *A61B 8/5207* (2013.01); *G06T 2207/10132* (2013.01)

(58) Field of Classification Search
CPC ........ G06T 2207/10132; A61B 6/5217; A61B 8/5223; A61B 5/004; A61B 6/5205
See application file for complete search history.

(56) References Cited

U.S. PATENT DOCUMENTS

2015/0002538 A1* 1/2015 Sohn .................... A61B 8/5223
345/629
2016/0110871 A1 4/2016 Kang et al.
(Continued)

FOREIGN PATENT DOCUMENTS

JP 2011167331 9/2011
JP 2014039852 3/2014
(Continued)

OTHER PUBLICATIONS

"International Search Report (Form PCT/ISA/210) of PCT/JP2021/030473," mailed on Oct. 5, 2021, with English translation thereof, pp. 1-5.
(Continued)

*Primary Examiner* — Gerald Johnson
(74) *Attorney, Agent, or Firm* — JCIPRNET

(57) ABSTRACT

An ultrasonography apparatus includes a processor configured to acquire an ultrasound image group including multiple ultrasound images of a subject captured by an ultrasound probe at multiple imaging positions of the subject, predict an imaging position where a disease predicted in the subject is capable of being imaged on the basis of the multiple ultrasound images of the subject with reference to multiple diagnosed ultrasound image groups and a diagnostic log which is for each of the multiple diagnosed ultrasound image groups and which includes positional information indicating a position of a disease, notify of the predicted imaging position, update the diagnostic log, detect a current position of the ultrasound probe on the subject, and display an image that shows the image of the subject superimposed with the current position of the ultrasound probe and the predicted imaging position on the image showing the image of the subject.

6 Claims, 6 Drawing Sheets

Related U.S. Application Data continuation of application No. PCT/JP2021/030473, filed on Aug. 19, 2021.

(56) References Cited

U.S. PATENT DOCUMENTS

| | | | |
|---|---|---|---|
| 2017/0215842 A1 | 8/2017 | Ryu et al. | |
| 2018/0360427 A1 | 12/2018 | Nakano et al. | |
| 2019/0200955 A1 | 7/2019 | Ryu et al. | |
| 2019/0295724 A1 | 9/2019 | Kanada | |
| 2020/0335216 A1* | 10/2020 | Ikezaki .................. | G16H 20/10 |
| 2023/0064623 A1 | 3/2023 | Krishnan et al. | |

FOREIGN PATENT DOCUMENTS

| | | |
|---|---|---|
| JP | 2017531455 | 10/2017 |
| JP | 2019000315 | 1/2019 |
| JP | WO2018116727 | 10/2019 |

OTHER PUBLICATIONS

"Written Opinion of the International Searching Authority (Form PCT/ISA/237) of PCT/JP2021/030473," mailed on Oct. 5, 2021, with English translation thereof, pp. 1-6.
"Notice of Reasons for Refusal of Japan Counterpart Application" with English translation thereof, issued on May 16, 2023, p. 1-p. 3.
"Office Action of Counterpart U.S. Appl. No. 18/173,071", issued on Aug. 1, 2024, pp. 1-18.
"Notice of Allowance of Counterpart U.S. Appl. No. 18/173,071", issued on Nov. 27, 2024, pp. 1-5.

* cited by examiner

FIG. 4
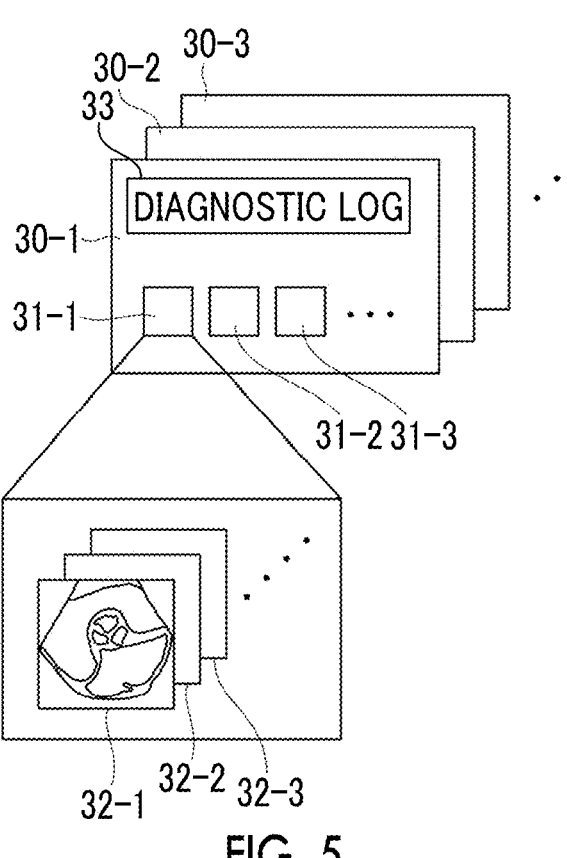
FIG. 5
DIAGNOSTIC LOG
INTRACARDIAC THROMBUS IS OBSERVED
AT DISTAL END OF CARDIAC APEX
FIG. 6
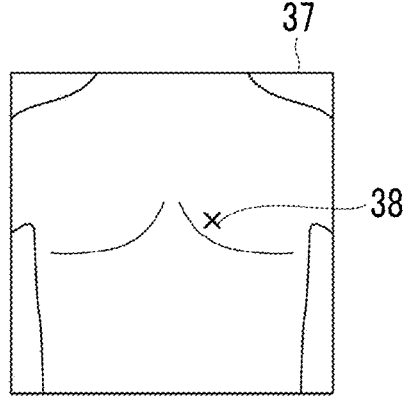

THROMBUS IS OBSERVED
IN LEFT AURICLE.

FIG. 9

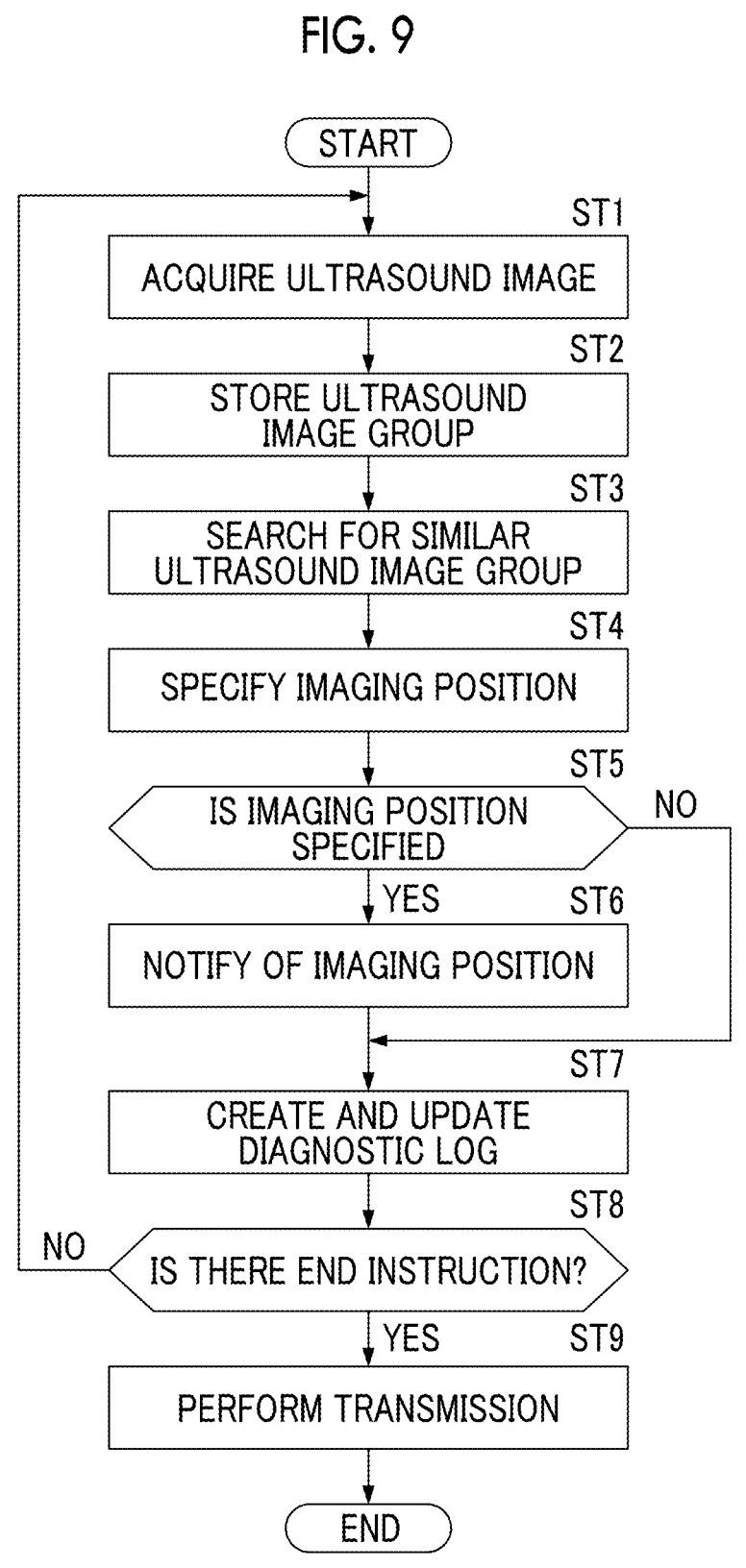

START

ST1
ACQUIRE ULTRASOUND IMAGE

ST2
STORE ULTRASOUND
IMAGE GROUP

ST3
SEARCH FOR SIMILAR
ULTRASOUND IMAGE GROUP

ST4
SPECIFY IMAGING POSITION

ST5
IS IMAGING POSITION
SPECIFIED
NO
YES
ST6
NOTIFY OF IMAGING POSITION

ST7
CREATE AND UPDATE
DIAGNOSTIC LOG

ST8
NO
IS THERE END INSTRUCTION?
YES
ST9
PERFORM TRANSMISSION

END

ULTRASONOGRAPHY APPARATUS, ULTRASONOGRAPHY METHOD, AND ULTRASONOGRAPHY PROGRAM FOR SHOWING IMAGE OF SUBJECT BASED ON ULTRASOUND PROBE

CROSS-REFERENCE TO RELATED APPLICATIONS

The present application is a continuation application of the pending U.S. application Ser. No. 18/173,071, filed on Feb. 23, 2023. The prior application Ser. No. 18/173,071 is a continuation of International Application No. PCT/JP2021/030473, filed on Aug. 19, 2021, which claims priority to Japanese Patent Application No. 2020-153150, filed on Sep. 11, 2020. Each application above is hereby expressly incorporated by reference, in its entirety, into the present application.

BACKGROUND

Technical Field

The present disclosure relates to an ultrasonography apparatus, an ultrasonography method, and an ultrasonography program.

Related Art

A similar case search device has been proposed that searches for a similar case image, which is similar to an image to be diagnosed, from a plurality of case images. For example, JP2014-039852A and JPWO2018-116727A1 propose a similar case search device that searches for a similar case including an image, which is similar to an image acquired by an ultrasonography apparatus or an endoscopic apparatus, a diagnostic log for the similar image, and the like.

However, JP2014-039852A and JPWO2018-116727A1 do not propose how to utilize the searched similar case for ultrasonography and how to improve the accuracy of ultrasound diagnosis.

SUMMARY OF THE INVENTION

The present disclosure has been made in view of the above circumstances, and an object of the present disclosure is to provide a technique that can use a similar case on an ultrasound image for ultrasonography to improve the accuracy of ultrasound diagnosis.

An ultrasonography apparatus according to the present disclosure includes at least one processor. The processor is configured to acquire an ultrasound image group including a plurality of ultrasound images of a subject captured by an ultrasound probe at a plurality of imaging positions of the subject, predict an imaging position where a disease predicted in the subject is capable of being imaged on the basis of the plurality of ultrasound images of the subject with reference to a plurality of diagnosed ultrasound image groups and a diagnostic log which is for each of the plurality of diagnosed ultrasound image groups and which includes positional information indicating a position of a disease, notify of the predicted imaging position, update the diagnostic log, detect a current position of the ultrasound probe on the subject, and display an image that shows the image of the subject superimposed with the current position of the ultrasound probe and the predicted imaging position on the image showing the image of the subject.

The "diagnosed ultrasound image group" means an ultrasound image group which has been subjected to diagnosis and for which a diagnostic log has been created.

In addition, in the ultrasonography apparatus according to the present disclosure, the processor may create a diagnostic log in which findings about the acquired ultrasound image group are described.

Further, in the ultrasonography apparatus according to the present disclosure, the processor could be configured to repeatedly perform the acquisition of a new ultrasound image group at the specified imaging position, the searching of a new similar ultrasound image group based on the new ultrasound image group, the specification of a new imaging position, and the notification of the new imaging position.

The term "based on a new ultrasound image group" means further based on a new ultrasound image group acquired at the specified imaging position in addition to a previously acquired ultrasound image group.

Furthermore, in the ultrasonography apparatus according to the present disclosure, the processor could be configured to repeatedly perform the acquisition of a new ultrasound image group at the specified imaging position, the searching of a new similar ultrasound image group based on the new ultrasound image group, the specification of a new imaging position, the notification of the new imaging position, and update of the diagnostic log based on findings about the new ultrasound image group.

An ultrasonography method according to the present disclosure includes acquiring an ultrasound image group including a plurality of ultrasound images of a subject captured by an ultrasound probe at a plurality of imaging positions of the subject; predicting an imaging position where a disease predicted in the subject is capable of being imaged on the basis of the plurality of ultrasound images of the subject with reference to a plurality of diagnosed ultrasound image groups and a diagnostic log which is for each of the plurality of diagnosed ultrasound image groups and which includes positional information indicating a position of a disease; notifying of the predicted imaging position; updating the diagnostic log; detecting a current position of the ultrasound probe on the subject; and displaying an image that shows image of the subject superimposed with the current position of the ultrasound probe and the predicted imaging position on the image schematically showing the image of the subject.

In addition, a program that causes a computer to execute the ultrasonography method according to the present disclosure may be provided.

According to the present disclosure, a similar case on an ultrasound image can be used for ultrasonography to improve the accuracy of ultrasound diagnosis.

BRIEF DESCRIPTION OF THE DRAWINGS

FIG. 4 is a diagram schematically illustrating a file configuration of a diagnosed ultrasound image group.

FIG. 5 is a diagram illustrating a diagnostic log for a similar ultrasound image group.

FIG. 6 is a diagram illustrating specification of an imaging position.

FIG. 9 is a flowchart illustrating a process performed in this embodiment.

DETAILED DESCRIPTION

Figure 1:
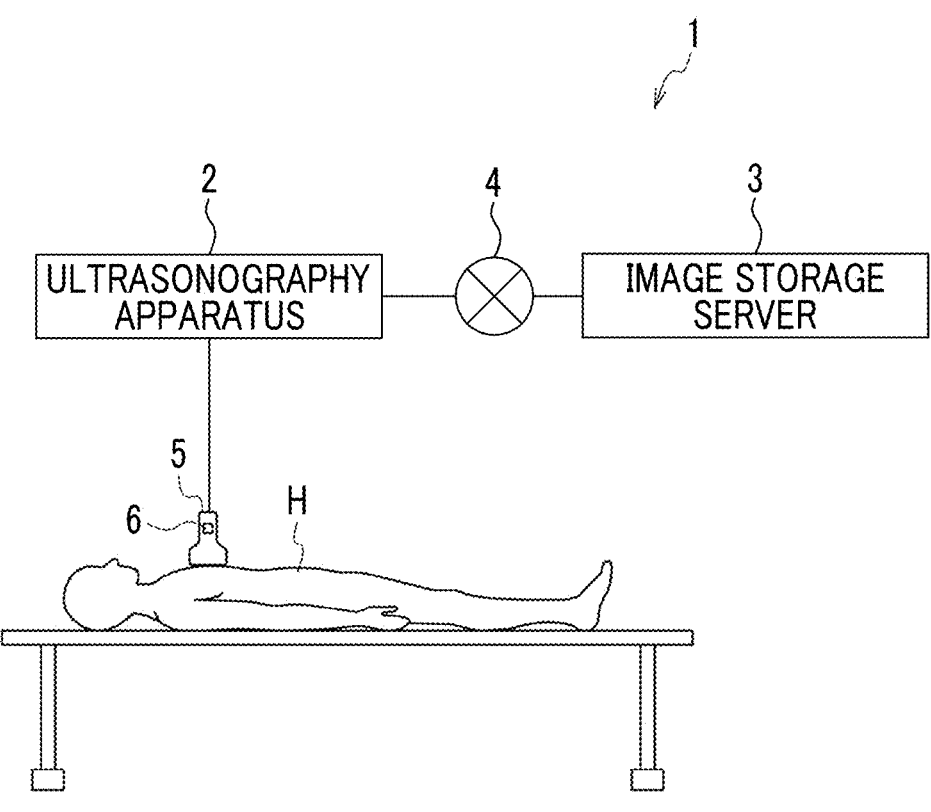
FIG. 1 is a diagram illustrating a schematic configuration of a medical information system to which an ultrasonography apparatus according to an embodiment of the present disclosure is applied.

Hereinafter, an embodiment of the present disclosure will be described with reference to the drawings. FIG. 1 is a hardware configuration diagram illustrating the outline of a diagnosis support system to which an ultrasonography apparatus according to the embodiment of the present disclosure is applied. As illustrated in FIG. 1, in a diagnosis support system 1, an ultrasonography apparatus 2 and an image storage server 3 according to this embodiment are connected to each other through a network 4 such that they can communicate with each other.

An ultrasound probe 5 is connected to the ultrasonography apparatus 2. The ultrasound probe 5 transmits ultrasonic waves to a part of a subject H to be measured in a state in which the ultrasound probe 5 is in contact with a body surface of the subject H, receives the ultrasonic waves reflected in the subject H, converts the received ultrasonic waves into an electric signal, and transmits the electric signal to the ultrasonography apparatus 2. The ultrasonography apparatus 2 images the received electric signal to acquire an ultrasound image. The ultrasound image is a tomographic image of a cross section which extends from an imaging position of the ultrasound probe 5 in a depth direction in the subject H.

The image storage server 3 is a computer that stores and manages various types of data and that comprises a high-capacity external storage device and database management software. The image storage server 3 communicates with the ultrasonography apparatus 2 through the wired or wireless network 4 to transmit and receive, for example, the ultrasound image acquired by the ultrasonography apparatus 2 and a diagnostic log using the ultrasound image created by the ultrasonography apparatus 2. The image storage server 3 stores the received ultrasound image, diagnostic log, and the like in a recording medium, such as a high-capacity external storage device, and manages them. In addition, the storage format of image data of the ultrasound image and the communication between the apparatuses through the network 4 are based on a protocol such as digital imaging and communication in medicine (DICOM). Further, the image storage server 3 is an example of an external device.

The ultrasound image and the diagnostic log are stored in the image storage server 3 in association with each other for each examination. In one examination, a plurality of ultrasound images are acquired as an ultrasound image group. Therefore, the diagnostic log is stored in the image storage server 3 in association with the ultrasound image group. Here, the plurality of ultrasound images stored in the image storage server 3 are used for diagnosis, and the diagnostic log is created. Therefore, in the following description, a plurality of ultrasound images acquired and stored in the image storage server 3 in one examination are referred to as a diagnosed ultrasound image group. In addition, one diagnosed ultrasound image group may include a sub-image group that consists of a plurality of ultrasound images acquired at different imaging positions on the body surface of the subject H.

Findings which are interpretation results of the ultrasound images by an examiner are described in the diagnostic log. The findings include information of, for example, the location of anatomical features and the type and size of diseases observed in the ultrasound image group. For example, in the case of an ultrasound image of a heart, findings including information indicating the anatomical features of the heart, such as the size of a left auricle, and the location of a disease, such as a thrombus, in a case in which the disease is observed in the ultrasound image are described in the diagnostic log. In addition, the diagnostic log is created by the ultrasonography apparatus 2.

Figure 2:
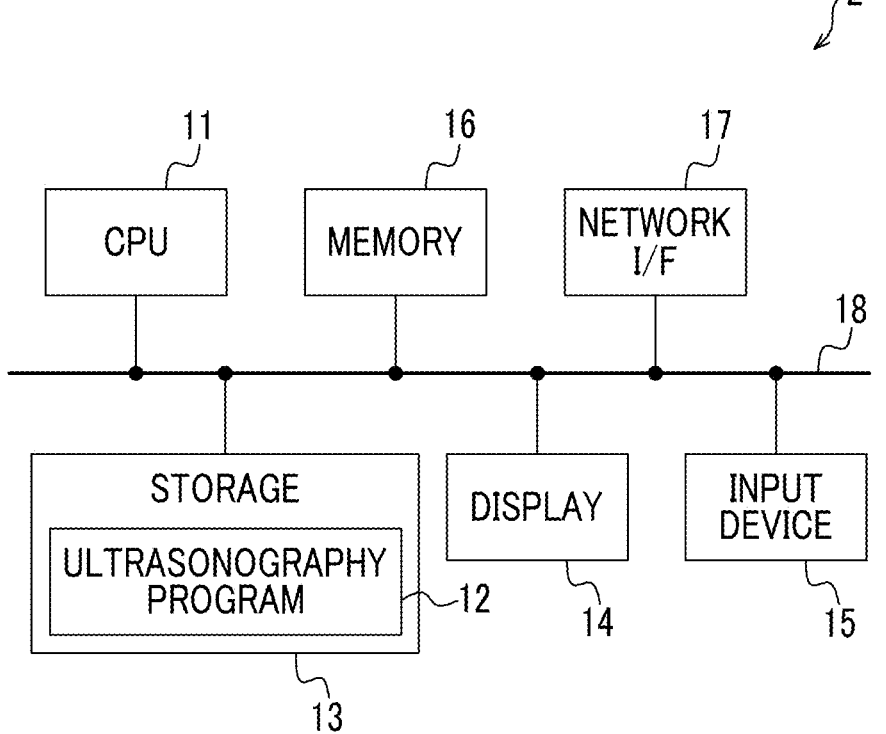
FIG. 2 is a diagram illustrating a schematic configuration of the ultrasonography apparatus according to this embodiment.

Next, the ultrasonography apparatus according to this embodiment will be described. FIG. 2 illustrates a hardware configuration of the ultrasonography apparatus according to this embodiment. As illustrated in FIG. 2, the ultrasonography apparatus 2 includes a central processing unit (CPU) 11, a non-volatile storage 13, and a memory 16 as a temporary storage area. In addition, the ultrasonography apparatus 2 includes a display 14, such as a liquid crystal display, an input device 15, such as a keyboard and a mouse, and a network interface (I/F) 17 that is connected to the network 4. The CPU 11, the storage 13, the display 14, the input device 15, the memory 16, and the network I/F 17 are connected to a bus 18. In addition, the CPU 11 is an example of a processor.

The storage 13 is implemented by, for example, a hard disk drive (HDD), a solid state drive (SSD), and a flash memory. An ultrasonography program 12 is stored in the storage 13 as a storage medium. The CPU 11 reads the ultrasonography program 12 from the storage 13, develops the ultrasonography program 12 in the memory 16, and executes the developed ultrasonography program 12.

Figure 3:
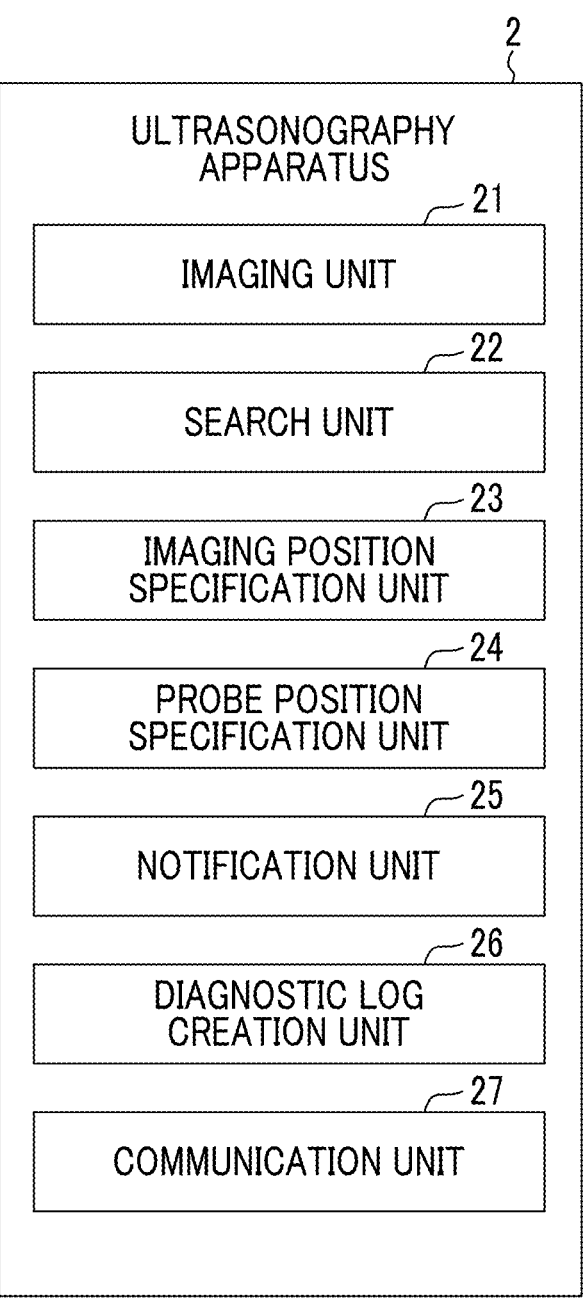
FIG. 3 is a diagram illustrating a functional configuration of the ultrasonography apparatus according to this embodiment.

Next, a functional configuration of the ultrasonography apparatus according to this embodiment will be described. FIG. 3 is a diagram illustrating the functional configuration of the ultrasonography apparatus according to this embodiment. As illustrated in FIG. 3, the ultrasonography apparatus 2 comprises an imaging unit 21, a search unit 22, an imaging position specification unit 23, a probe position specification unit 24, a notification unit 25, a diagnostic log creation unit 26, and a communication unit 27. The CPU 11 executes the ultrasonography program 12 to function as the imaging unit 21, the search unit 22, the imaging position specification unit 23, the probe position specification unit 24, the notification unit 25, the diagnostic log creation unit 26, and the communication unit 27.

The imaging unit 21 images the electric signals input from the ultrasound probe 5, which is moved along the body surface of the subject H, at a predetermined frame rate (for example, 30 fps) and sequentially acquires a plurality of ultrasound images. In addition, the imaging unit 21 stores, as an ultrasound image group, a plurality of ultrasound images acquired for a period from the start of storage to the end of the storage in the storage 13 in response to storage start and end instructions input by the examiner through the input device 15. In this case, the acquired ultrasound image group is stored as one image file in the storage 13 in association with an examination ID for specifying the examination that is currently being performed. In addition, the ultrasound image group for the examination that is currently being performed is referred to as an ultrasound image group during diagnosis.

The search unit 22 searches for a similar ultrasound image group that is similar to the features of the ultrasound image group during diagnosis acquired by the imaging unit 21 with reference to the image storage server 3. FIG. 4 is a diagram schematically illustrating a file configuration of a plurality of diagnosed ultrasound image groups stored in the image storage server 3. As illustrated in FIG. 4, a plurality of diagnosed ultrasound image groups 30-1, 30-2, 30-3, . . . are stored in the image storage server 3. One diagnosed ultrasound image group includes a plurality of ultrasound images acquired in one examination. In one examination, a plurality of ultrasound images are acquired at different imaging positions. Therefore, one diagnosed ultrasound image group includes a plurality of sub-image groups 31-1, 31-2, 31-3, . . . that include a plurality of ultrasound images acquired at different imaging positions. In addition, FIG. 4 illustrates that the sub-image group 31-1 includes a plurality of ultrasound images 32-1, 32-2, 32-3, . . . . In addition, a diagnostic log 33 for the examination is associated with one diagnosed ultrasound image group. In FIG. 4, the diagnostic log 33 is illustrated to be included in the diagnosed ultrasound image group. However, the diagnostic log and the diagnosed ultrasound image group may be stored as separate files in the image storage server 3.

Further, in this embodiment, one diagnosed ultrasound image group may constitute one image file. In this case, the number of ultrasound images in the diagnosed ultrasound image group, the number of ultrasound images in each of the sub-image groups, and the imaging date and time of each of the sub-image groups are described in a tag of the image file. Meanwhile, each of the plurality of sub-image groups may constitute one image file, and the plurality of sub-image groups may be stored in a folder for one examination.

The search unit 22 specifies the features of the ultrasound image group during diagnosis in order to search for a similar ultrasound image group. For example, the number of ultrasound images included in the ultrasound image group during diagnosis, anatomical features included in a plurality of ultrasound images, and the plurality of ultrasound images can be used as the features of the ultrasound image group during diagnosis.

Here, the ultrasound image group during diagnosis is stored as one image file consisting of a plurality of ultrasound images in the storage 13. Tag information is given to the image file. For example, the imaging date and time of the ultrasound image group during diagnosis and the number of images are described in the tag information. The search unit 22 acquires the number of ultrasound images included in the ultrasound image group during diagnosis with reference to the tag information given to the image file of the ultrasound image group during diagnosis. In addition, in some cases, for a specific disease, a larger number of ultrasound images are acquired as compared to other diseases. Therefore, the number of ultrasound images is a feature for the ultrasound image group.

Further, the search unit 22 performs a region detection process on the ultrasound images included in the ultrasound image group during diagnosis to detect anatomical features included in a plurality of ultrasound images. Furthermore, the search unit 22 has a trained model, such as a neural network, which has been subjected to machine learning to detect anatomical features included in the heart, a liver, a kidney, blood vessels, and the like and detects the anatomical features included in the ultrasound images using the trained model. In addition, the search unit 22 may perform template matching using a template that indicates the shape of the anatomical features included in the heart, the liver, the kidney, the blood vessels, and the like to specify the anatomical features, instead of using the trained model. In addition, the search unit 22 may detect the anatomical features from only one ultrasound image included in the ultrasound image group during diagnosis. However, in a case in which the anatomical features are detected from only one ultrasound image, the accuracy of detecting the anatomical features may be low. Therefore, the anatomical features may be detected from some of the plurality of ultrasound images.

The search unit 22 compares the number of ultrasound images included in the ultrasound image group during diagnosis with the number of ultrasound images included in each of the plurality of diagnosed ultrasound image groups stored in the image storage server 3 or with the number of ultrasound images included in each of the sub-image groups constituting the diagnosed ultrasound image group and derives a similarity that has a larger value as the difference between the numbers of ultrasound images becomes smaller as a first similarity S1 with the diagnosed ultrasound image group or with the sub-image group. For example, the reciprocal of (the absolute value of the difference between the numbers of ultrasound images+1) can be used as the first similarity S1. In a case in which the difference between the numbers of ultrasound images is 0, the first similarity S1 is 1 which is the maximum value. In addition, in this embodiment, the search unit 22 compares the number of ultrasound images included in the ultrasound image group during diagnosis with the number of ultrasound images included in the sub-image group constituting the diagnosed ultrasound image group. However, the present disclosure is not limited thereto.

Further, the search unit 22 specifies a diagnosed ultrasound image group, in which anatomical features matched with the anatomical features detected for the ultrasound image group during diagnosis are described in the diagnostic log, with reference to the diagnostic log for each of the plurality of diagnosed ultrasound image groups stored in the image storage server 3. Furthermore, the search unit 22 derives a second similarity based on a correlation value between the ultrasound images included in the ultrasound image group during diagnosis and the ultrasound images included in each of the plurality of diagnosed ultrasound image groups. For example, the search unit 22 registers each of the ultrasound images included in the ultrasound image group during diagnosis with each of the ultrasound images included in the diagnosed ultrasound image group or the sub-image group and derives, as the correlation value, the absolute value of the difference between the pixel values of the corresponding pixels of both images after the registration. Then, the search unit 22 normalizes the correlation value to a value of 0 to 1 to derive the second similarity S2. In addition, the search unit 22 derives the second similarity S2 based on the correlation value between the ultrasound image included in the ultrasound image group during diagnosis and the ultrasound image included in the sub-image group constituting the diagnosed ultrasound image group. However, the present disclosure is not limited thereto.

The search unit 22 calculates the sum S1+S2 of the first and second similarities for the diagnosed ultrasound image group, in which the anatomical features matched with the anatomical features detected for the ultrasound image group during diagnosis are described in the diagnostic log, and sorts the diagnosed ultrasound image groups in descending order of the sum S1+S2. Then, the search unit 22 searches for a predetermined number of (one or more) diagnosed ultrasound image groups having the largest sum S1+S2 as the similar ultrasound image groups. In addition, the search unit 22 may search for the similar ultrasound image group using only the first similarity S1 or only the second similarity S2.

The imaging position specification unit 23 specifies the imaging position on the body surface of the subject H where a disease predicted in the subject H can be imaged, using positional information indicating the position of the disease included in the diagnostic log for the similar ultrasound image group. That is, the imaging position specification unit 23 determines whether or not a disease name is included, with reference to the diagnostic logs for all of the searched similar ultrasound image groups. In a case in which the disease name is included, a description of positional information indicating the position of the disease is included in the diagnostic log. Therefore, in a case in which the disease name is included in the diagnostic log for the similar ultrasound image group, the imaging position specification unit 23 acquires the disease name and the positional information from the diagnostic log. In a case in which the disease name is not included in the diagnostic logs for all of the searched similar ultrasound image groups, the imaging position specification unit 23 does not specify the imaging position.

FIG. 5 is a diagram illustrating a diagnostic log for a certain similar ultrasound image group. As illustrated in FIG. 5, "Intracardiac thrombus is observed at the distal end of the cardiac apex" is described in a diagnostic log 35. In this case, the imaging position specification unit 23 acquires "intracardiac thrombus" as the disease name and information of "the distal end of the cardiac apex" as the positional information from the diagnostic log 35. Therefore, the occurrence of the intracardiac thrombus at the distal end of the cardiac apex is predicted in the subject H from the diagnostic log 35 for the similar ultrasound image group.

Further, the imaging position specification unit 23 specifies the position on the body surface of the subject H where the disease predicted in the subject H can be imaged, using the positional information acquired from the diagnostic log 35. FIG. 6 is a diagram illustrating the specification of the position on the body surface of the subject H where anatomical features can be imaged. In addition, here, it is assumed that the positional information acquired from the diagnostic log 35 is the "distal end of the cardiac apex". As illustrated in FIG. 6, the imaging position specification unit 23 specifies an imaging position 38 where the distal end of the cardiac apex can be imaged in a schema 37 which is an image schematically illustrating a chest of the subject H.

The probe position specification unit 24 specifies the current position of the ultrasound probe 5 on the body surface of the subject. In this embodiment, as illustrated in FIG. 1, a sensor 6 that detects the position of the ultrasound probe 5 is attached to the ultrasound probe 5. The sensor 6 is a 6-axis sensor that detects a moving direction, orientation, and rotation of the ultrasound probe 5 and that calculates a moving distance, a moving speed, and the like. Specifically, the 6-axis sensor is implemented by a combination of an acceleration sensor that can detect three directions of a front-rear direction, a left-right direction, and an up-down direction and a geomagnetic sensor that can detect north, south, east, and west or by a combination of an acceleration sensor and a gyro sensor that can detect the speed of rotation.

The probe position specification unit 24 acquires the current position of the ultrasound probe 5 on the body surface of the subject H on the basis of output information from the sensor 6.

In addition, instead of the 6-axis sensor, such as the sensor 6, the magnetic sensor described in JP2011-167331A may be used. In addition, a marker that can detect a position in the directions of three axes in a space may be attached to the ultrasound probe 5, and a captured image of the marker may be analyzed to specify the position of the ultrasound probe 5. Further, a method for specifying the position of the ultrasound probe 5 is not limited thereto, and any method can be used.

Figure 7:
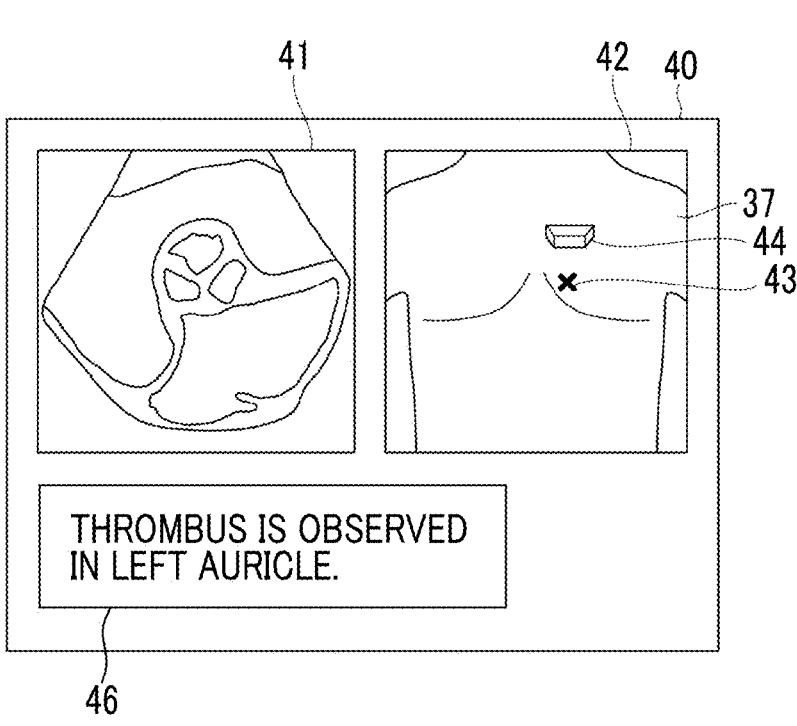
FIG. 7 is a diagram illustrating a notification screen.

The notification unit 25 notifies the examiner of the imaging position specified by the imaging position specification unit 23. Specifically, the notification unit 25 notifies of the imaging position by displaying the schema which schematically shows the body surface of the subject H on the display 14 and superimposing the current position of the ultrasound probe 5 and the imaging position on the displayed schema. FIG. 7 is a diagram illustrating an imaging position notification screen. As illustrated in FIG. 7, a notification screen 40 has a first image region 41 and a second image region 42. An ultrasound image that is currently being captured is displayed in the first image region 41. The schema 37 illustrated in FIG. 6 is displayed in the second image region 42. A mark 43 is superimposed on the schema 37 at the imaging position 38 illustrated in FIG. 6. Further, in addition to the mark 43, an icon 44 indicating the ultrasound probe 5 is displayed at the current position of the ultrasound probe 5 specified by the probe position specification unit 24. In addition, a findings region 46 in which the examiner describes findings about the ultrasound image group is displayed on the notification screen 40. The examiner can input the findings about the ultrasound image group to the findings region 46 using the input device 15.

The examiner can see the notification screen 40 to visually recognize at a glance how the ultrasound probe 5 can be moved to the imaging position where a disease is expected.

The diagnostic log creation unit 26 describes the findings, which have been input to the findings region 46 by the examiner, in the diagnostic log to create the diagnostic log. For example, in FIG. 7, since "a thrombus is observed in the left auricle" is input as the findings, the diagnostic log creation unit 26 describes "a thrombus is observed in the left auricle" in the diagnostic log.

In addition, in this embodiment, whenever the imaging position is notified of, the ultrasound image group is acquired at each of a plurality of imaging positions on the body surface of the subject H. Therefore, in this embodiment, whenever a new ultrasound image group is acquired, the search unit 22 searches for a new similar ultrasound image group. For example, in a case in which the examiner moves the ultrasound probe 5 to the imaging position indicated by the mark 43 to acquire a new ultrasound image group, the search unit 22 searches for a new similar ultrasound image group, using the previously acquired ultrasound image group and the new ultrasound image group. In this case, there is a high probability that the new similar ultrasound image group searched for on the basis of the features of the new ultrasound image group will include the ultrasound image obtained by imaging a part which is different from that in the previous similar ultrasound image group. Therefore, there is a high probability that the diagnostic log of the new similar ultrasound image group will include a disease which is not included in the diagnostic log of the previous similar ultrasound image group. Therefore, the imaging position specification unit 23 can specify a new imaging position, where a predicted disease can be imaged, with reference to the diagnostic log of the new similar ultrasound image group. Then, the notification unit 25 notifies of the new imaging position such that the examiner can move the ultrasound probe 5 to the new imaging position to further acquire a new ultrasound image group. The newly acquired ultrasound image group becomes an ultrasound image group during diagnosis at the new imaging position.

Figure 8:
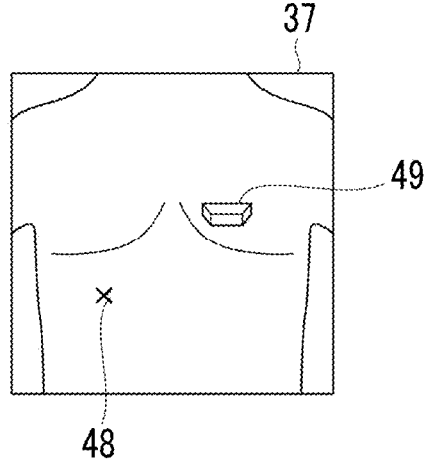
FIG. 8 is a diagram illustrating the specification of a new imaging position.

For example, it is assumed that the diagnostic log of the searched similar ultrasound image group includes a description of a disease related to the liver in a case in which the ultrasound probe 5 is moved to the imaging position indicated by the mark 43 illustrated in FIG. 7 to acquire an ultrasound image. In this case, the imaging position specification unit 23 specifies the liver at the imaging position. Therefore, as illustrated in FIG. 8, a mark 48 indicating a new imaging position is superimposed on the notification screen 40 at the position of the liver in the schema 37. In addition, an icon 49 indicating the current position of the ultrasound probe 5 is displayed in FIG. 8. Therefore, it is possible to acquire the ultrasound image of the subject H at the position where the ultrasound image could not be captured in only the previous similar ultrasound image group and to check whether or not a disease occurs.

In addition, in a case in which the findings about the new ultrasound image group are input to the findings region 46, the diagnostic log creation unit 26 updates a diagnostic log. For example, in a case in which the ultrasound probe 5 is moved to the imaging position indicated by the mark 43 illustrated in FIG. 7 to acquire a new ultrasound image group, the examiner inputs findings about the new ultrasound image group to the findings region 46 of the notification screen 40. In a case in which findings based on the new ultrasound image group are input to the findings region 46, the diagnostic log creation unit 26 adds the input findings to the diagnostic log to update the diagnostic log.

In a case in which the examiner inputs an instruction to end the examination, the communication unit 27 generates one diagnosed ultrasound image group having, as a sub-image group, each of a plurality of ultrasound image groups acquired at each of a plurality of imaging positions and transmits the one diagnosed ultrasound image group to the image storage server 3 together with the diagnostic log described up to the end of the examination. The image storage server 3 stores the transmitted diagnosed ultrasound image group and diagnostic log as a new diagnosed ultrasound image group.

Next, a process performed in this embodiment will be described. FIG. 9 is a flowchart illustrating the process performed in this embodiment. The process is started in response to the input of an examination start instruction, and the imaging unit 21 sequentially acquires ultrasound images (Step ST1) and stores an ultrasound image group including a plurality of ultrasound images acquired between a storage start instruction and a storage end instruction from the examiner in the storage 13 (Step ST2).

Then, the search unit 22 searches for a similar ultrasound image group that is similar to the features of the acquired ultrasound image group with reference to the image storage server 3 (Step ST3). Then, the imaging position specification unit 23 specifies the imaging position on the body surface of the subject where the disease predicted in the subject can be imaged, using the diagnostic log for the similar ultrasound image group (Step ST4). In a case in which the imaging position is specified (Step ST5; YES), the notification unit 25 notifies of the specified imaging position (Step ST6).

In a case in which the determination result in Step ST5 is "NO" and following Step ST6, the diagnostic log creation unit 26 receives the input of findings by the examiner and describes the input findings in the diagnostic log to create the diagnostic log (Step ST7). Then, it is determined whether or not an end instruction is input (Step ST8). In a case in which the determination result in Step ST8 is "NO", the process returns to Step ST1. Then, the processes from Step ST1 to Step ST7 are repeated. In a case in which the determination result in Step ST8 is "YES", the communication unit 27 derives one diagnosed ultrasound image group having, as sub-image groups, the ultrasound image groups during diagnosis acquired at each of the specified imaging positions, and transmits the diagnosed ultrasound image group and the diagnostic log to the image storage server 3 (Step ST9). Then, the process is ended. Further, in a case in which the processes from Step ST1 to Step ST7 are repeated, the diagnostic log creation unit 26 updates the diagnostic log in the process in Step ST7.

As described above, in this embodiment, a similar ultrasound image group that is similar to the features of the ultrasound image group during diagnosis is searched for, and the imaging position on the body surface of the subject where the disease predicted in the subject can be imaged is specified using the positional information of the disease included in the diagnostic log for the similar ultrasound image group. Then, the specified imaging position is notified of. Therefore, the operator can move the ultrasound probe 5 to the notified of imaging position, acquire an ultrasound image group, and interpret the acquired ultrasound image group to check whether or not a disease occurs. Therefore, it is possible to acquire an ultrasound image without overlooking a disease, using the similar ultrasound image group. As a result, it is possible to improve the accuracy of ultrasound diagnosis.

In addition, the acquisition of a new ultrasound image group at the specified imaging position, the searching of a new similar ultrasound image group based on the new ultrasound image group, the specification of a new imaging position, the notification of the new imaging position, and the update of the diagnostic log based on findings about the new ultrasound image group can be repeatedly performed to acquire the ultrasound image of the subject at a position where the ultrasound image could not be captured in only the similar ultrasound image group and to check whether or not a disease occurs. Therefore, it is possible to examine the disease that is likely to occur, without omission.

Figure 10:
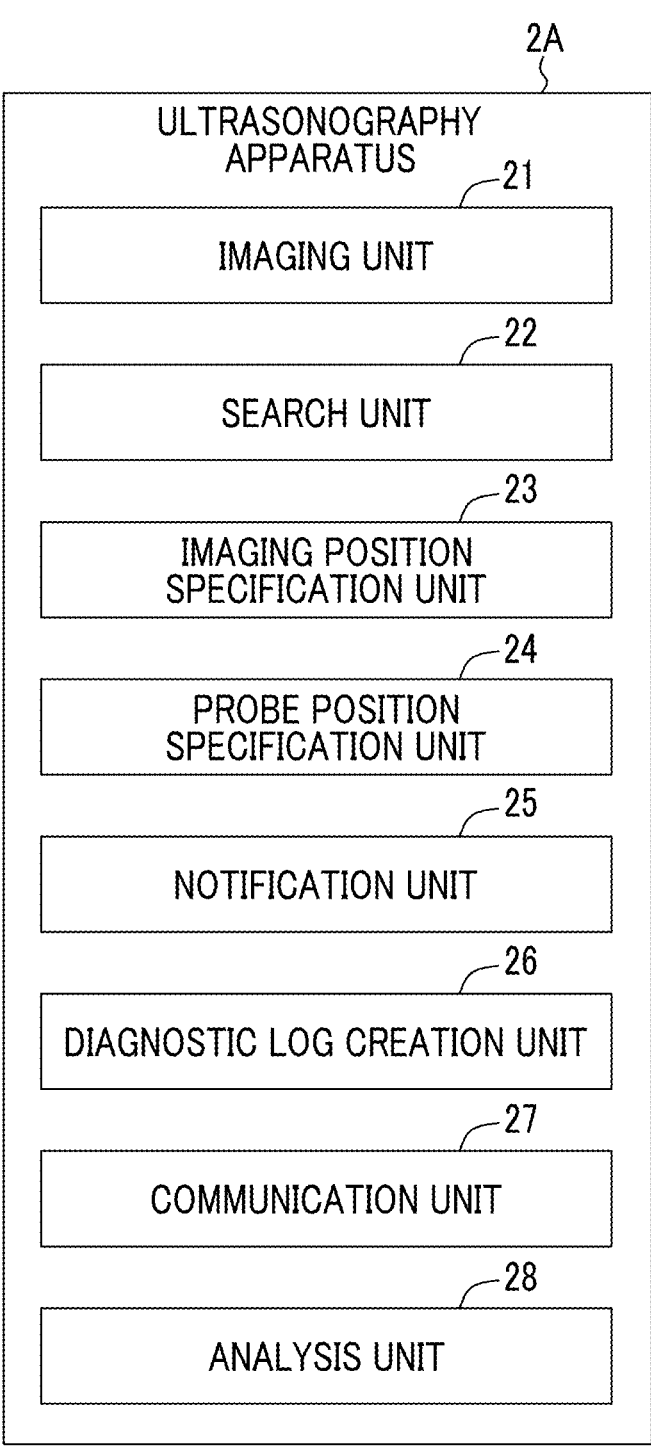
FIG. 10 is a diagram illustrating a functional configuration of an ultrasonography apparatus according to another embodiment.

In addition, the ultrasonography apparatus according to this embodiment may include an analysis unit 28 that analyzes an ultrasound image group to detect an abnormal shadow from the ultrasound image group, like another ultrasonography apparatus 2A according to this embodiment illustrated in FIG. 10. The analysis unit 28 analyzes an ultrasound image group to detect an abnormal shadow, such as a disease, included in the ultrasound image group. The analysis unit 28 detects shadows of a plurality of types of diseases as abnormal shadows from the ultrasound image group using a known computer-aided diagnosis (that is, CAD) algorithm.

As described above, since the ultrasonography apparatus 2A according to this embodiment includes the analysis unit 28, it is possible to display an analysis result on the notification screen 40 or to describe the analysis result in the diagnostic log. Therefore, it is possible to efficiently perform a diagnosis using the ultrasound image group.

In addition, in the above-described embodiments, for example, the following various processors can be used as a hardware structure of processing units performing various processes, such as the imaging unit 21, the search unit 22, the imaging position specification unit 23, the probe position specification unit 24, the notification unit 25, the diagnostic log creation unit 26, the communication unit 27, and the analysis unit 28. The various processors include, for example, a CPU which is a general-purpose processor executing software (programs) to function as various processing units as described above, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or by a combination of two or more processors of the same type or different types (for example, a combination of a plurality of FPGAs or a combination of a CPU and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As described above, various processing units are configured by one or more of the various processors as a hardware structure.

In addition, specifically, an electric circuit (circuitry) obtained by combining circuit elements, such as semiconductor elements, can be used as the hardware structure of the various processors.

What is claimed is:

1. An ultrasonography apparatus comprising:
an ultrasound probe; and
at least one processor,
wherein the processor is configured to:
acquire an ultrasound image group including a plurality of ultrasound images of a subject captured by the ultrasound probe at a plurality of imaging positions of the subject;
predict an imaging position where the imaging position has not been detected and a disease predicted in the subject is capable of being imaged on the basis of the plurality of ultrasound images of the subject with reference to a plurality of diagnosed ultrasound image groups and a diagnostic log which is for each of the plurality of diagnosed ultrasound image groups and which includes positional information indicating a position of a disease;
notify of the predicted imaging position;
update the diagnostic log;
detect a current position of the ultrasound probe on the subject; and
display an image that shows the image of the subject superimposed with the current position of the ultrasound probe and the predicted imaging position on the image showing the image of the subject.

2. The ultrasonography apparatus according to claim 1, wherein the processor is configured to create the diagnostic log in which findings about the acquired ultrasound image group are described.

3. The ultrasonography apparatus according to claim 1, wherein the processor is configured to repeatedly perform the acquisition of a new ultrasound image group at the predicted imaging position, the searching of a new similar ultrasound image group based on the new ultrasound image group, a specification of a new imaging position based on the predicted imaging position, and the notification of the new imaging position.

4. The ultrasonography apparatus according to claim 2, wherein the processor is configured to repeatedly perform the acquisition of a new ultrasound image group at the predicted imaging position, the searching of a new similar ultrasound image group based on the new ultrasound image group, a specification of a new imaging position based on the predicted imaging position, the notification of the new imaging position, and update of the diagnostic log based on findings about the new ultrasound image group.

5. An ultrasonography method used by an ultrasonography apparatus having a processor and an ultrasonic probe, the method comprising:
acquiring an ultrasound image group including a plurality of ultrasound images of a subject captured by the ultrasound probe at a plurality of imaging positions of the subject;
predicting an imaging position where the imaging position has not been detected and a disease predicted in the subject is capable of being imaged on the basis of the plurality of ultrasound images of the subject with reference to a plurality of diagnosed ultrasound image groups and a diagnostic log which is for each of the plurality of diagnosed ultrasound image groups and which includes positional information indicating a position of a disease;
notifying of the predicted imaging position;
updating the diagnostic log;
detecting a current position of the ultrasound probe on the subject; and
displaying an image that shows image of the subject superimposed with the current position of the ultrasound probe and the predicted imaging position on the image schematically showing the image of the subject.

6. A non-transitory computer-readable storage medium that stores an ultrasonography program that causes an ultrasonography apparatus having a processor and an ultrasonic probe to execute:
acquiring an ultrasound image group including a plurality of ultrasound images of a subject captured by the ultrasound probe at a plurality of imaging positions of the subject;
predicting an imaging position where the imaging position has not been detected and a disease predicted in the subject is capable of being imaged on the basis of the plurality of ultrasound images of the subject with reference to a plurality of diagnosed ultrasound image groups and a diagnostic log which is for each of the plurality of diagnosed ultrasound image groups and which includes positional information indicating a position of a disease;
notifying of the predicted imaging position;
updating the diagnostic log;
detecting a current position of the ultrasound probe on the subject; and displaying an image that shows the image of the subject superimposed with the current position of the ultrasound probe and the predicted imaging position on the image schematically showing the image of the subject.

* * * * *